United States Patent
Lamoreaux

(10) Patent No.: US 8,398,965 B2
(45) Date of Patent: Mar. 19, 2013

(54) SCENTED SOIL FOR HUNTING AND TRAPPING

(76) Inventor: Michael Lamoreaux, Crossville, TN (US)

( * ) Notice: Subject to any disclaimer, the term of this patent is extended or adjusted under 35 U.S.C. 154(b) by 118 days.

(21) Appl. No.: 12/883,207

(22) Filed: Sep. 16, 2010

(65) Prior Publication Data

US 2011/0002878 A1    Jan. 6, 2011

Related U.S. Application Data

(63) Continuation-in-part of application No. 11/698,354, filed on Jan. 26, 2007, now abandoned.

(60) Provisional application No. 60/762,448, filed on Jan. 26, 2006.

(51) Int. Cl.
*A01N 25/00* (2006.01)
(52) U.S. Cl. .......................................... 424/84
(58) Field of Classification Search ........................ None
See application file for complete search history.

(56) References Cited

PUBLICATIONS

MSDS, Alson Corporation, "Paraffin Wax" (1995).*
MSDS, Enkaustikos! Wax Art Supplies, "Soy Wax" (2009).*
Silicate ceramics [obtained on Apr. 6, 2012], obtained from the internet <URL:www.vscht.cz/sil/keramika/Ceramic_Technology/SM-Lect-6A.pdf>.*

* cited by examiner

*Primary Examiner* — James H. Alstrum-Acevedo
*Assistant Examiner* — Frank Choi
(74) *Attorney, Agent, or Firm* — Hornkohl Intellectual Property Law, PLLC; Jason L. Hornkohl

(57) ABSTRACT

The present invention is directed toward a wax and scent impregnated soil for use in hunting and trapping. The soil is dried and mixed with wax and a scent such as the urine of a target species. The wax makes the soil water resistant and prevents it from freezing. In addition, the wax increases the ability of the soil to retain the impregnated scent over a period of time. The soil is used to attract various animals to traps or target hunting areas. Alternatively, the soil can be spread around to disguise the scent of a hunter or trapper such that they are not detected by the animals they are pursuing. A repellant version can be made by using a repellant scent.

7 Claims, 3 Drawing Sheets

SCENTED SOIL FOR HUNTING AND TRAPPING

CROSS-REFERENCES TO RELATED APPLICATIONS

This application is a Non-Provisional Utility Application which is a Continuation-in-Part of and claims priority from U.S. patent application Ser. No. 11/698,354 filed Jan. 26, 2007 now abandoned and entitled "SCENTED SOIL FOR HUNTING AND TRAPPING" which claimed priority from U.S. Provisional Patent Application Ser. No. 60/762,448 filed Jan. 26, 2006 and entitled "SCENTED SOIL FOR HUNTING AND TRAPPING" which are both hereby incorporated by reference.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND OF THE INVENTION

Many species of animals use a scent-based, territorial marking system for reproduction such as deer, elk, moose, bear, boar, etc. Animals that detect another animal's scent in an area may be attracted to, or repelled from, the area if the scent indicates that a potential adversary or mate is in the area. In addition, natural animal scents may disguise human odors that might alert an animal to a human's presence and, thus, frighten or scare the animal away. Many hunters know the importance of using animal scents to attract animals and disguise human odors when hunting or trapping. Unfortunately, many available scents disperse quickly or are washed away by rain and lose their effectiveness over time. Thus, new scent must be regularly applied to maintain an effect amount of scent in the target area. Therefore, what is needed is an improved method and product for introducing a desired longer lasting scent into a target area.

BRIEF SUMMARY OF THE INVENTION

An embodiment of the present invention is directed toward a mixture for use in attracting or repelling an animal. The mixture includes a dried substrate or soil, a coating substance and a scent bearing material. The coating substance is mixed with the dried substrate or soil and the scent bearing material such that a substantially waterproof, granular, scented soil is created. The coating substance is preferably a wax and the scent bearing material is preferably deer urine, although any desired scent may be used. The wax is melted and mixed with the substrate and the urine in a substantially contaminate free environment until the wax solidifies creating a granular material. Finally, the granular material is vacuum packed in an airtight container filled with an inert gas to maintain its freshness and potency.

Another embodiment of the present invention is directed toward an animal attractant or repellant. The attractant or repellant includes a granular substrate, a natural animal scent obtained from an animal, such as urine, and a wax-like material such as paraffin.

Yet another embodiment of the present invention is directed toward a method of producing an animal attractant or repellant. In accordance with the method, a granular substrate is produced by grinding and sifting a raw substrate. The substrate is then dried to remove most of the moisture in the substrate. The processed substrate is then impregnated with a scented material such as deer urine. The scented substrate is mixed, in a substantially contaminate free environment, with a waterproofing material such as a wax. The wax and scented substrate are heated and then cooled while being mixed. The processed product is then preferably vacuum packed in an air tight package.

DETAILED DESCRIPTION OF THE INVENTION

A preferred embodiment of the present invention is directed toward a method of producing a solid mixture that is impregnated with urines and gland secretions of various species of animals which will not absorb moisture or freeze into a stiff mass. The scented mixture remains loose and granulated while holding the scent for a lengthy period of time and, thus, is ideal for outdoor use when hunting or trapping. The scent is preferably a urine and/or gland secretion of a desired species of animal. The scent is also preferably obtained during the mating season of the desired species of animal (for example, deer). The preferred mixture is comprised of a sifted soil, deer urine and gland secretions and paraffin wax. The soil and wax are preferably heated and mixed together in a sequence of urine, soil, urine, wax, urine, wax, urine that is continuously mixed until cooled.

Figure 1:
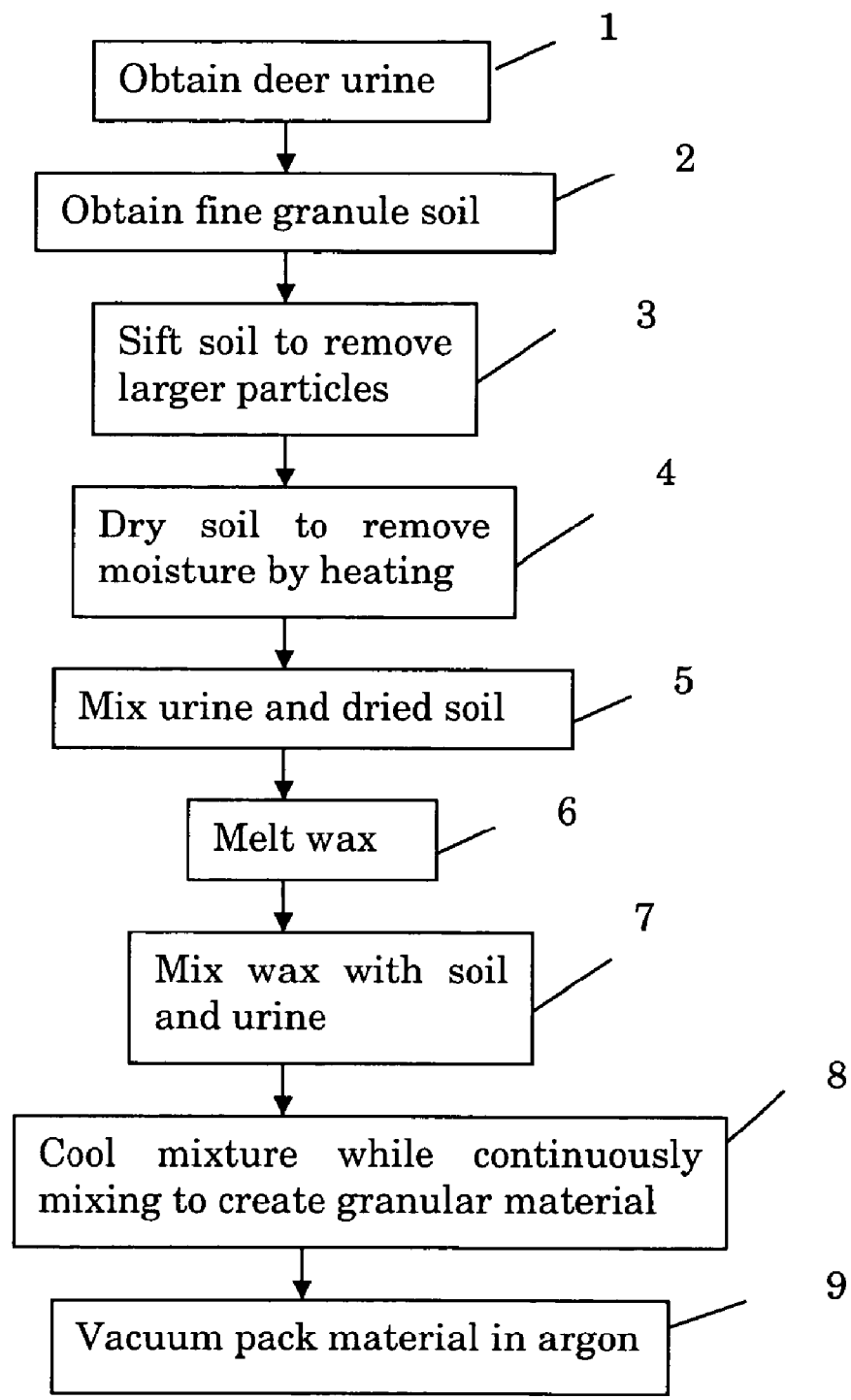
FIG. 1 is a flowchart of a method of creating a scented soil in accordance with an embodiment of the present invention.

Referring now to FIG. 1 a method of creating a scented soil in accordance with an embodiment of the present invention is shown. The method commences in step 1 with the obtaining of a scented material. The product preferably uses 100% natural urine and gland secretions of the desired species of animals. These natural scents disguise the scent of a hunter or trap and lure the animal to the desired location. However, synthetic or artificial scents may be used if desired.

In step 2, a fine, granular soil is obtained. The soil is preferably sifted to remove any larger particles as shown in step 3. Preferably, a ⅜" screen is used to sift a loamy type soil to provide a fine granule soil. Sandy soil is not desirable as it will not absorb the scent as readily as a loamy soil or clay. The sifted soil is then dried in step 4 to remove any moisture that may be present. The soil moisture content should be as close to 0% as possible to create a dusty, dry soil. In the preferred method, the soil is dried by heating the soil to a temperature between approximately 165 to 180 degrees Fahrenheit. Over heating should be avoided since this may cause scorching of the soil which leaves an undesirable odor and discoloration. Overly heated soil may also cause the applied urine or scent to dissipate on contact which is undesirable. The scented material, deer urine in the preferred embodiment of FIG. 1, is mixed with the dried soil in step 5. In accordance with the preferred method, the soil is removed from the heating instrument and immediately placed in a plastic lined or a ploy-coated container that is preheated to 80-100 degrees Fahrenheit. Metal containers are not preferred for mixing the soil and urine due to the fact that 1) heated metal causes urine to dissipate; and 2) metal has a chemical reaction to urine. However, stainless steel or other types of suitable metal containers can be used if care is taken to avoid these problems. Conversely, plastic containers allow the urine to be worked into soil without the soil being affected by the container or the container by the soil.

In step 6, a wax is melted which is then mixed with the soil and urine is step 7. In step 8, the wax, soil and scented material are continuously mixed while the mixture cools to create a granular material. Wax is added to the soil to make it water resistant and increase its ability to retain the applied scent. The wax is preferably applied to the soil at the rate of approximately one-sixteenth pound wax per one pound of soil. Paraffin wax is preferred although any wax-like material can be used. Soy wax, a natural product made from soy beans, is also effective. The wax is heated to a temperature of approximately 250-300° Fahrenheit such that the wax melts into a liquid form. In accordance with a preferred method for manufacturing the scented soil, urine is added to the soil at a ratio of two ounces of urine per pound of soil. To begin the process, approximately one-half ounce of urine is sprayed in a misting manner into the heated container prior to placing the heated soil into the container. The heated soil is then placed into the container and mixed thoroughly with the urine. Another one-half ounce of urine is then sprayed in a misting manner into the soil and mixed thoroughly. Seventy-five to eighty percent of the wax is then mixed thoroughly into soil. Next, another three-fourths of an ounce of urine is sprayed in a misting manner and mixed into soil thoroughly. The remaining 20-25% of wax is then thoroughly mixed with the soil. The remaining quarter ounce of urine is then sprayed in a misting manner into the soil and mixed thoroughly. The soil, wax and urine mixture is preferably mixed continuously throughout the process as the urine is added. Once all of the urine and wax has been added to the soil, the mixture is continually mixed until cooled. While the above process is preferred, it will be readily appreciated that the order of some steps can be altered without substantially altering the final product or departing from the scope of the present invention.

The impregnating of urine and gland secretions into the soil, combined with the prevention of moisture absorption and freezing of the soil due to the wax coating, extends the longevity of the scented soil when used in the field. This allows the hunter or trapper to minimize contact with, and thus the presence of human scent in, the designated target area. Human scent is undesirable in designated target areas because it alarms animals and deters them from entering the target areas. Thus, the presence of human scent reduces the hunter's or trapper's opportunities to pursue and harvest the animals.

Finally, in step 9, the granular material is vacuum packed in an inert gas such as argon. The wax and urine impregnated soil is preferably prepared, cooled and kept in a non-contaminated cooling area that is free of all undesirable odors and particles that may contaminate the product and be detected by the olfactory senses of a target animal. Once completely cooled, the soil is vacuum packed in airtight packaging to further minimize any possible contamination. The package may be filled with an inert gas to preserve the scent of the soil overtime. The soil can then be used to attract a desired animal or disguise human odors when hunting and trapping.

The product should be manufactured and handled in a manner that minimizes the growth of bacteria or mildew. The drying/sterilizing, vacuum packaging and inert gas all serve to minimize the growth of mildew or bacteria on the product. In addition, a growth inhibitor such as an antibiotic may be added to the mixture to further inhibit the growth of bacteria or mildew.

Figure 2:
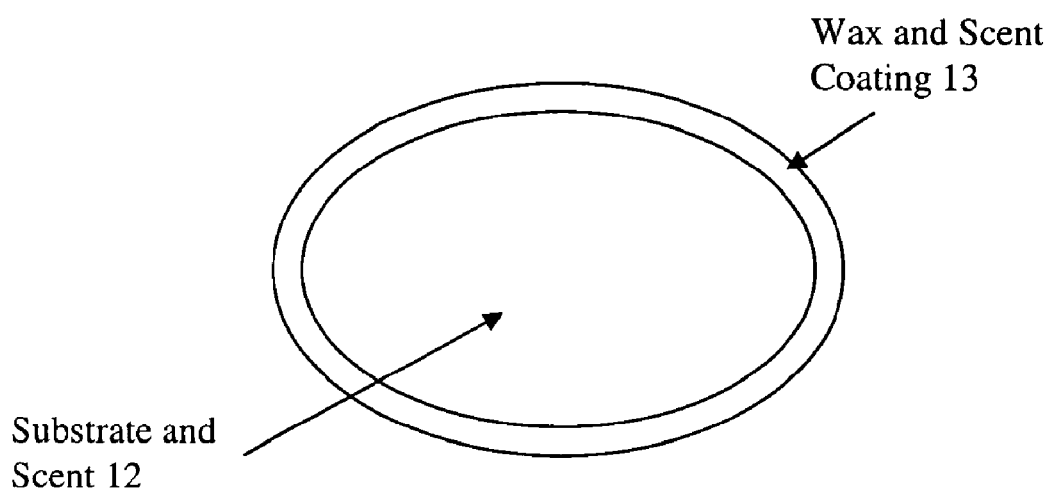
FIG. 2 is an illustration of an ideal scented, substantially waterproof particle created in accordance with an embodiment of the present invention.

An ideal scented, substantially waterproof particle created in accordance with an embodiment of the present invention is shown in FIG. 2. The particle consists of a scent and substrate core 12 surrounded by a scent impregnated wax coating. The wax/scent coating 13 makes the material substantially waterproof and slows the release of the scent from the substrate core 12. Those skilled in the art will recognize that a product constructed in accordance with the above described method will not consist solely of ideal particles.

The present invention can be used to attract many species of animals that use a scent-based, territorial marking system for reproduction such as deer, elk, moose, bear, boar, pig, turkey, etc. Because these animals' olfactory senses are extremely sensitive, the scented soil created in accordance with the present invention preferably uses the animal's own urine and gland secretions to scent the soil. However, synthetic scents can be used for economical reasons if desired. For example, a turkey attractant can be constructed using the method described herein with oyster shell grit, anise oil and Iodine added to attract the turkeys. To ensure that the target animal does not detect a human or unfamiliar odor in the scented soil, it is critical that the soil be handled such that it is not contaminated with extraneous odors or bacteria during the manufacturing process. However, once the scented soil is placed in the target animal's natural environment, it can be freely exposed to the environment since any additional odors picked up by the soil will be odors that the animal is already accustomed to smelling.

Figure 3:
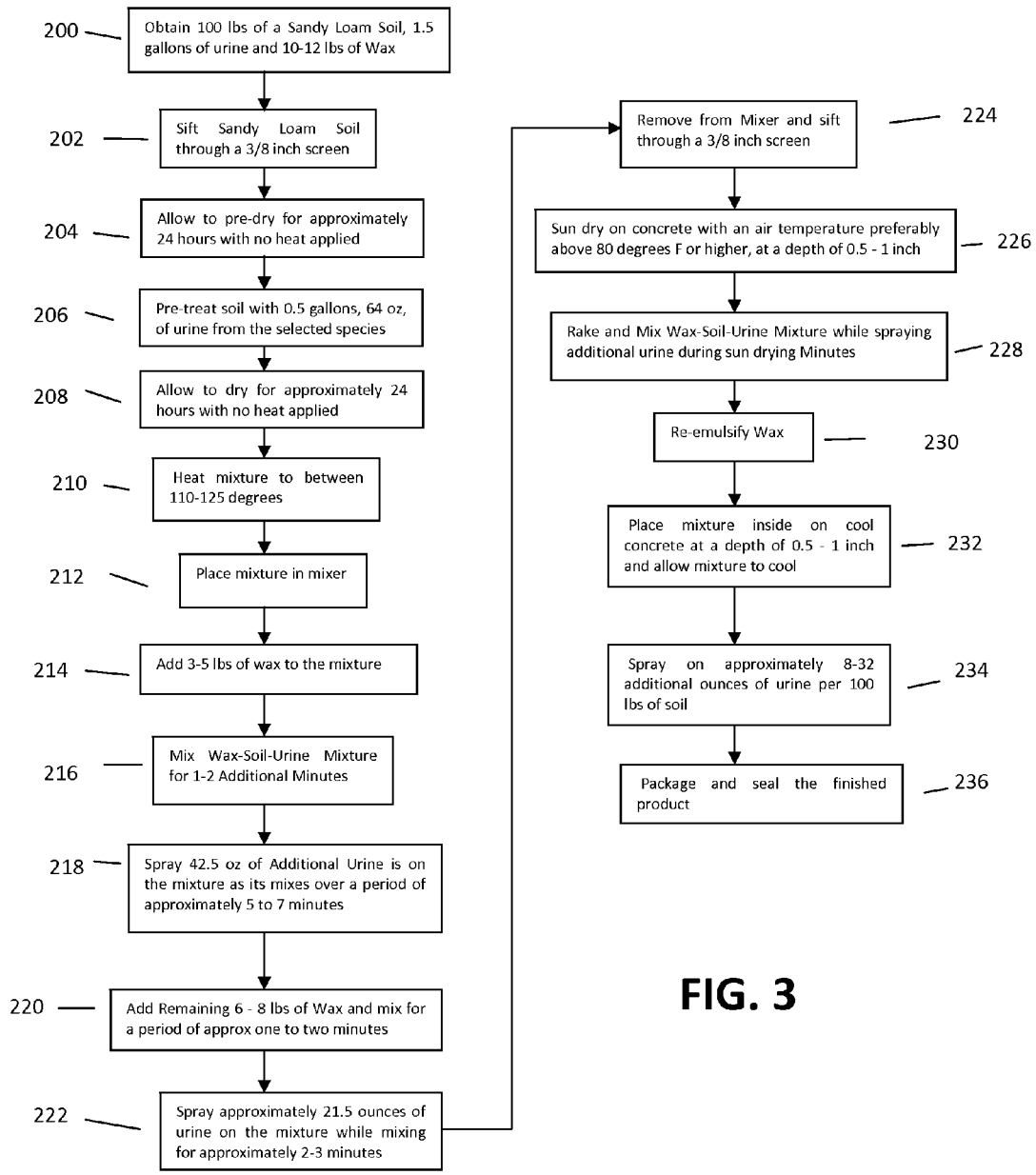
FIG. 3 is a flowchart of an especially preferred method of manufacturing an animal attractant from a sandy loam soil in accordance with an embodiment of the present invention.

Referring now to FIG. 3, an especially preferred method of manufacturing an animal attractant from a sandy loam soil in accordance with an embodiment of the present invention is shown. The ingredients for the batch are 100 lbs of a sandy loam soil, 1.5 gallons of urine as discussed above, and 10-12 lbs of wax. In the embodiment of FIG. 3, the method begins in step 200 with the obtaining of the specified ingredients. The sandy loam soil is first sifted through a ⅜ inch screen in step 202. The soil is then allowed to pre-dry in step 204 for a period of about 24 hours. In step 206, the sifted loam is pretreated with 0.5 gallons, 64 oz, of urine from the selected species. The pre-treated soil is then again allowed to dry for approximately 24 hours with no heat applied in step 208. This helps the urine better permeate the sifted soil and also allows the urine to begin to break down and causes a slight odor of ammonia which further spurs the curiosity of the subject animals. The amount of urine used during the no heat pre-treatment is preferably is ⅓ (64 oz in the example of FIG. 3) of the total urine (urine, gland or synthetic) mixture to be used in the mixture.

After the expiration of the 24 hour period, the mixture is heated to between 110-125 degrees Fahrenheit in step 210. In step 212, as soon as the desired temperature has been reached, the mixture is placed in a mixer. 3-5 lbs of wax is then added to the mixture in step 214. The wax-soil-urine mixture is then mixed for 1-2 additional minutes in step 216. In step 218, 42.5 oz of additional urine is sprayed on the mixture as its mixes over a period of approximately 5 to 7 minutes. Next, in step 220, the remaining 6-8 lbs of wax are added to mixer and mixed for a period of approx one to two minutes. The remaining 21.5 ounces of urine are then sprayed on the mixture while mixing during an additional approximately 2-3 minutes period, step 222.

The soil is removed from the mixer immediately after the mixing process is complete, step, and re-sifted through a ⅜$^{th}$ inch screen in step 224. The sifted soil in then spread on a warm concrete surface, on sunny days only with an air temperature preferably above 80 degrees F. or higher, at a depth of 0.5-1 inch to sun dry in step 226. As shown in step 228, while the mixture is sun drying, it should be raked or mixed soil 3-4 times and with each rake/mix, an additional spray of urine added, for a total of approximately 10-20 oz of additional urine solution per 100 lbs of soil. The sun drying helps eliminate artificial scents that may result from the process and detected by the target animal. The additional urine adds to the layering of the scent. The mixture is left in the sun for approx 2-3 hours or until wax has re-emulsified allowing a through penetration into the soil as shown in step 230.

The soil mixture is then brought into a building and spread on a cool concrete floor overnight at a depth of 0.5-1 inch in step 232. The cool concrete only not cools soil but draws heat from soils and most importantly any condensation (moisture) from the soil. After the soil is cooled it is enhanced by a final light spraying of urine, approximately 8-32 additional ounces of urine per 100 lbs of soil, with a raking or mixing of the soil after each spraying in step 234 immediately prior to sacking and sealing in step 236.

While the above requirements might not be deemed necessary by those unskilled in scented soils, the present inventor has found them, through thorough experimentation in the lab and research in the field, to be strongly preferred by the animals they are designed to attract. The key is to create the most interesting scent possible for the animal and the above process creates layers of odors that have been observed to be preferred. The ratio of the ingredients in the mixture strongly affects the response of the animals to the scented soil. In addition, the above timing schedule is absolutely crucial to prevent the wax from clumping up the soil as it cools, thereby rendering the mixture difficult to use and strong differences in the attractiveness of the scented soil have been observed to result from the timing While the present invention is primarily discussed with regard to attracting target animals, it will be appreciated by those skilled in the art that the present invention can be easily adapted to repelling undesirable animals by impregnating the soil with a scent that is alarming or repulsive to the target animals. For example, wolf urine, hot pepper oil, egg whites and blood meal can be used to repel deer. In addition, the protective coating process described herein can be used to slow the release of pesticides citronella or other natural insect repellents that are spread on the ground to kill or repel insects such as mosquitoes, fire-ants, Ticks, etc. Thus, although there have been described particular embodiments of the present invention of a new and useful SCENTED SOIL FOR HUNTING AND TRAPPING, it is not intended that such references be construed as limitations upon the scope of this invention except as set forth in the following claims.

What is claimed is:

1. A method of producing an animal attractant, comprising:
   (a) providing a sandy loam soil;
   (b) drying the sandy loam soil to remove to moisture;
   (c) mixing animal urine with the dried sandy loam to produce a soil-urine mixture;
   (d) melting a paraffin or soy wax to produce a melted wax;
   (e) heating the soil-urine mixture to between 110-125 degrees Fahrenheit;
   (f) mixing the melted wax with the soil-urine mixture to produce a soil-urine-wax mixture;
   (g) cooling the soil-urine-wax mixture to room temperature;
   (h) drying the soil-urine-wax mixture until the wax emulsifies; and
   (i) cooling the soil-urine-wax mixture while mixing and spraying urine on the soil-urine-wax mixture to produce said animal attractant.

2. The method of claim 1 wherein step (a) further comprises sifting the sandy loam soil.

3. The method of claim 1 wherein step (b) further comprises heating the soil to a temperature between approximately 165 to 180 degrees F.

4. The method of claim 1 wherein step (d) further comprises the wax to a temperature between approximately 250 to 300 degrees F.

5. The method of claim 1 further comprising vacuum packing the animal attractant in an air tight package.

6. The mixture of claim 1 wherein the animal attractant contains said paraffin or soy wax at a ratio of approximately one-sixteenth pound of said paraffin or soy wax per pound of sandy loam soil.

7. The method of claim 1 further comprising packing the animal attractant in a sealed package substantially filled with an inert gas.

\* \* \* \* \*